United States Patent [19]

Van Overloop

[11] Patent Number: 4,525,091
[45] Date of Patent: * Jun. 25, 1985

[54] SCRUB SPONGE WITH OPPOSED PUNCTURE MEMBER ARMS

[75] Inventor: Ronald R. Van Overloop, Palatine, Ill.

[73] Assignee: The Kendall Company, Boston, Mass.

[*] Notice: The portion of the term of this patent subsequent to Sep. 4, 2001 has been disclaimed.

[21] Appl. No.: 488,519

[22] Filed: Apr. 25, 1983

[51] Int. Cl.³ .................. B43K 5/14; A45D 40/26
[52] U.S. Cl. .................. 401/134; 401/196; 132/88.7; 604/3
[58] Field of Search ............ 401/132, 133, 134, 135, 401/196; 222/80, 81, 83, 83.5, 85, 86, 88, 89, 90, 91, 105, 106; 604/1, 2, 3, 403, 408, 416, 244, 411, 412, 413, 414, 415; 132/88.7

[56] References Cited

U.S. PATENT DOCUMENTS

| | | | |
|---|---|---|---|
| 2,209,914 | 7/1940 | Gerber et al. | 401/196 |
| 3,248,754 | 5/1966 | Mario | 401/132 |
| 3,636,922 | 1/1972 | Ketner | 401/132 |
| 3,998,559 | 12/1976 | Hoyt | 401/132 |
| 4,027,985 | 6/1977 | Loesser | 401/134 |
| 4,112,944 | 9/1978 | Williams | 604/244 |
| 4,117,841 | 10/1978 | Perrotta | 401/132 |
| 4,148,318 | 4/1979 | Meyer | 401/132 |
| 4,291,697 | 9/1981 | Georgevich | 401/132 |
| 4,330,220 | 5/1982 | Schaar et al. | 401/134 |
| 4,415,288 | 11/1983 | Gordon et al. | 401/132 |
| 4,469,463 | 9/1984 | Overloop | 401/134 |

Primary Examiner—Hugh R. Chamblee
Assistant Examiner—Carolyn A. Harrison
Attorney, Agent, or Firm—Powell L. Sprunger

[57] ABSTRACT

A scrub sponge comprising, a packet having a rupturable wall and a closed chamber containing a liquid scrub agent, and a cover of foam material having a cavity to receive the packet and enclosing the packet. The sponge has a puncture member intermediate the cover and the packet and having a pair of generally aligned and spaced arms on opposed sides of the packet beneath the cover, and hinge means connecting the arms adjacent one end of the packet. The puncture member has at least one sharp projection on one of the arms directed toward the packet to pierce the wall when the arms are pressed toward each other to release the scrub agent into the cover, and an opening extending through the one arm adjacent the projection.

16 Claims, 4 Drawing Figures

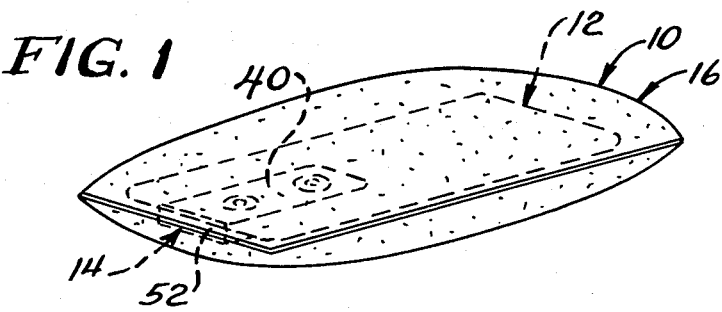
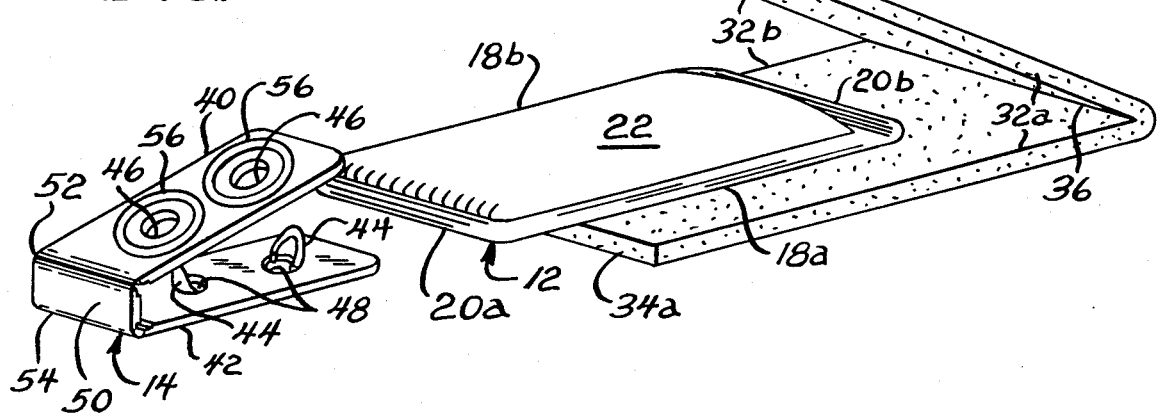
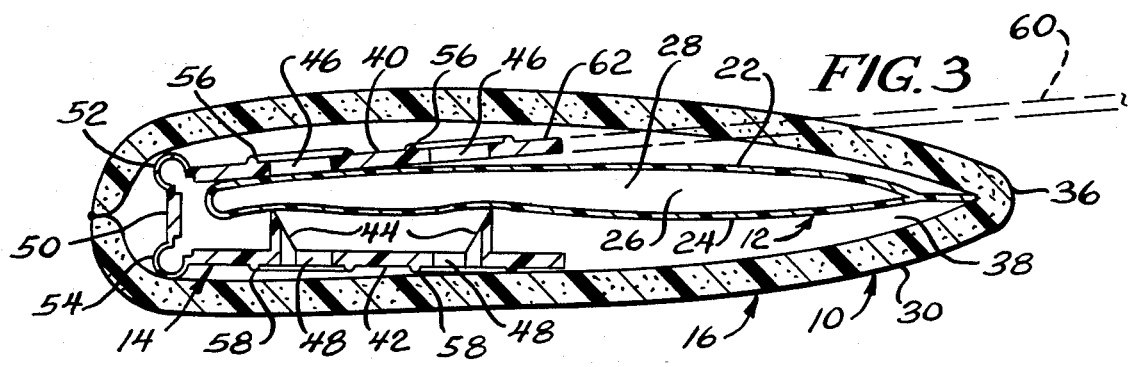
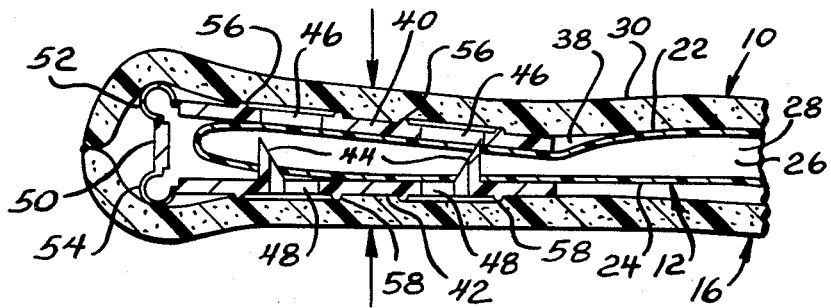

SCRUB SPONGE WITH OPPOSED PUNCTURE MEMBER ARMS

CROSS-REFERENCE TO RELATED APPLICATION

Ser. No. 488,520 filed Apr. 25, 1983.

BACKGROUND OF THE INVENTION

The present invention relates to surgical devices, and more particularly to scrub sponges.

Prior to surgery, the operative site is cleaned by hospital personnel in order to minimize the possibility of contamination around the site. First, a scrub solution comprising a soap or detergent is utilized to wash the patient in the region of the operative site after which the scrub solution is removed from the patient. Next, the patient is painted with an antiseptic liquid, such as povidone iodine, in the region of the site. When dry the antiseptic paint provides a continuous protective film in the region of the site, and surgery is ready to commence.

A scrub sponge is disclosed in U.S. Pat. No. 4,330,220, incorporated herein by reference, which includes a puncture member on one side of a rupturable packet. However, it has been discovered that when a projection on the puncture member pierces the packet it may pass through the sponge and scratch the patient when the sponge is used, which of course is undesirable.

SUMMARY OF THE INVENTION

A principal feature of the present invention is the provision of an improved sponge of simplified construction for scrubbing procedures.

The scrub sponge of the present invention comprises, a packet having a rupturable wall and a closed chamber containing a liquid scrub agent, and a cover of foam material having a cavity to receive the packet and enclosing the packet. The sponge has a puncture member intermediate the cover and the packet and having a pair of generally aligned and spaced arms on opposed sides of the packet beneath the cover, and hinge means connecting the arms adjacent one end of the packet. The puncture member has at least one sharp projection on one of the arms directed toward the packet, and an opening extending through the one arm adjacent the projection.

A feature of the present invention is that the projection pierces the puncturable walls when the arms are pressed toward each other.

Another feature of the invention is that the pierced walls release the scrub agent from the packet.

Yet another feature of the invention is that both sides of the packet may be ruptured by the one arm to release the scrub agent from both sides of the packet.

Still another feature of the invention is that the opening permits passage of the scrub agent into the cover.

Yet another feature of the invention is that the cover retains the scrub agent in a position for easy placement on the patient.

Thus, a feature of the present invention is that the scrub agent may be released and applied to the patient in a simplified manner.

A further feature of the invention is that the opposed arms prevent the projection from scratching the patient during use of the sponge.

Further features will become more fully apparent in the following description of the embodiments of this invention and from the appended claims.

DESCRIPTION OF THE DRAWINGS

In the drawings:

FIG. 1 is a perspective view of a scrub sponge of the present invention;

FIG. 2 is an exploded view of the scrub sponge of FIG. 1;

FIG. 3 is a sectional view illustrating the sponge prior to puncture of a packet in the sponge; and FIG. 4 is a fragmentary sectional view illustrating the sponge after the packet has been pierced by a puncture member.

DESCRIPTION OF THE PREFERRED EMBODIMENTS

Referring now to FIGS. 1-4, there is shown a scrub sponge generally designated 10 having a packet 12, a puncture member 14, and a cover 16. The packet 12 has a pair of side edges 18a and 18b, and a pair of end edges 20a and 20b connecting the side edges 18a and b. The packet 12 has a front wall 22 and a back wall 24 which are joined at their periphery to define a chamber 26 intermediate the front and back walls 22 and 24. The front and back walls 22 and 24 are made from a puncturable material, such as a lamination of metallic foil and heat sealable plastic, such that the edges of the front and back walls 22 and 24 may be heat sealed together to form the chamber 26. The packet 12 contains a liquid scrub agent 28 in the chamber 26, such as a solution of soap or detergent with or without povidone iodine, or a solution containing an antiseptic agent, such as povidone iodine.

The cover 16 preferably comprises an absorbent and porous foam material, such as polyurethane foam. In a preferred form, the cover 16 comprises an elongated strip 30 having a pair of side edges 32a and 32b, and a pair of end edges 34a and 34b connecting the side edges 32a and b. The strip 30 is folded about a fold line 36 at a longitudinal central portion of the strip, such that the end edges 34a and 34b are located adjacent each other when the strip 30 is folded. The side edge 32a of the strip 30 intermediate fold line 36 and the end edges 34a and b are joined together by suitable means, such as by heat sealing, the side edge 32b intermediate the fold line 36 and the end edges 34a and b are joined together by suitable means, such as by heat sealing, and the end edges 34a and b are joined together by suitable means, such as by heat sealing. In this manner, the joined edges of the strip 30 define a cavity 38 to receive the packet 12, with the width of the packet between the side edges 18a and b being approximately equal to the width of the cavity 38, and with the length of the packet 12 intermediate the end edges 20a and b being approximately equal to the length of the cavity 38. In this configuration, the side edge 18a of the packet 12 is located adjacent the side edge 32a of the cover 16, the side edge 18b of the packet 12 is located adjacent the side edge 32b of the cover 16, the end edge 20a of the packet 12 is located adjacent the joined end edges 34a and b of the cover 16, and the end edge 20b of the packet 12 is located adjacent the fold line 36 of the cover 16.

The puncture member 14 may be formed from a flexible plastic material, such as polypropylene. As shown, the puncture member 14 is located intermediate the cover 16 and the packet 12. The puncture member 14 has a pair of generally aligned and spaced arms 40 and 42 on opposed sides of the packet 12 beneath the cover 16. The one arm 42 has a pair of spaced sharp projections 44 directed toward the packet 12, and the other arm 40 has a pair of spaced openings 46 aligned with the projections 44. The arm 42 has a pair of openings 48 located adjacent the projections 44. The puncture member 14 has a hinge 50 connecting one end of the arms 40 and 42 with the hinge 50 having a pair of spaced lateral flexible regions 52 and 54 adjacent the arms 40 and 42 to permit movement of the arms 40 and 42 toward each other. The projections 44 are tapered to a sharp point for a purpose which will be described below.

With reference to FIG. 3, the arms 40 and 42 are located on opposed sides of the packet 12, and the hinge 50 is located adjacent one end of the packet 12. The arms 40 and 42 are located in a first spaced position such that the projections 44 do not pierce the packet 12 prior to use of the sponge 10. However, with reference to FIG. 4, when it is desired to use the sponge 10, the arms 40 and 42 are pressed toward each other to a second close position such that the projections 44 pierce the opposed walls of the packet 12. After the walls have been pierced, the scrub agent 28 passes through the walls on opposed sides of the packet 12 and through the openings 46 and 48 into the cover 16 in order to impregnate the cover for use of the sponge 10 on a patient. As shown, the projections 44 on the arm 42 are aligned with the openings 46 on the arm 40, such that the openings 46 receive the projections 44. However, when the arms 40 and 42 are pressed to their second close position, the projections 44 do not pass through the arm 40 in order to prevent scratching the patient during use of the sponge 10 by the projections 44. As shown, the arms 40 and 42 may have raised rings 56 and 58 surrounding the openings 46 and 48, respectively, such that the user may feel the rings 56 and 58 through the cover 16 in order to locate the region of the projections 44 and openings 46.

In accordance with the present invention, a scrub sponge 10 may be used with an agent 28 which may either be detergent or povidone iodine mixed with the detergent in order to initially scrub the site of surgery for a quick kill of bacteria in the region of the site. Also, the sponge 10 may be utilized with an agent 28 of povidone iodine in order to paint the surgery site after the scrub has been completed for a long term kill of bacteria in the site. For this procedure, with reference to FIG. 3, the sponge 10 preferably has an elongated handle 60 extending from an outer end 62 of the arm 40 and passing through an opening in the cover 16 in order to hold the sponge 10 by the handle 60 while performing the paint procedure.

The foregoing detailed description is given for clearness of understanding only, and no unnecessary limitations should be understood therefrom, as modifications will be obvious to those skilled in the art.

I claim:
1. A scrub sponge, comprising:
a packet having a rupturable wall and a closed chamber containing a liquid scrub agent;
a cover of foam material having a cavity to receive said packet and enclosing said packet; and
a puncture member intermediate said cover and the packet and having a pair of generally aligned and spaced arms on opposed sides of the packet beneath the cover, hinge means connecting said arms adjacent one end of the packet, and at least one sharp projection on one of said arms directed toward the packet to pierce the wall when the arms are pressed toward each other to release the scrub agent into the cover, and an opening extending through the other arm and aligned with the projection.

2. The sponge of claim 1 wherein said cover comprises an elongated sheet having a pair of opposed side edges and a pair of opposed end edges connecting the side edges, with said sheet being folded along a line at a longitudinal central portion of the sheet intermediate said end edges, said side edges intermediate the fold line and end edges being joined together, and said end edges being joined together to define the cavity.

3. The sponge of claim 2 wherein said packet has a pair of opposed side edges, and a pair of opposed end edges connecting the side edges, with one of the packet end edges being located adjacent the joined end edges of the cover, with the other packet end edge being located adjacent the cover fold line, and with the packet side edges being located adjacent the joined side edges of the cover.

4. The sponge of claim 1 wherein said cover comprises a polyurethane foam.

5. The sponge of claim 1 wherein the walls of said packet comprise a metallic foil.

6. The sponge of claim 1 wherein said scrub agent comprises povidone iodine.

7. The sponge of claim 1 wherein said scrub agent comprises a detergent.

8. The sponge of claim 1 wherein said puncture member comprises a flexible plastic material.

9. The sponge of claim 1 wherein said projection is tapered toward a relatively sharp point.

10. The sponge of claim 1 wherein said packet has a width and length substantially the width and length of said cavity.

11. The sponge of claim 1 wherein the one arm has an opening extending therethrough adjacent said projection.

12. The sponge of claim 11 wherein the other of said arms includes an opening extending therethrough and aligned with the projection.

13. The sponge of claim 12 including a raised ring extending around the openings on the one and other arms on a surface of the arms remote from the packet.

14. The sponge of claim 1 wherein said one arm includes a pair of spaced sharp projections directed toward the packet.

15. The sponge of claim 14 wherein the other of said arms includes a pair of openings extending therethrough and aligned with the projections.

16. The sponge of claim 11 including a raised ring extending around the opening on a surface of the one arm remote the packet.

* * * * *